United States Patent [19]

Micheler

[11] Patent Number: 5,725,500
[45] Date of Patent: Mar. 10, 1998

[54] CONTAINERS FOR LIQUID MEDICAMENTS

[75] Inventor: Clemens Micheler, Planegg, Germany

[73] Assignee: Eli Lilly and Company, Indianapolis, Ind.

[21] Appl. No.: 652,078

[22] Filed: May 23, 1996

[30] Foreign Application Priority Data

Jun. 2, 1995 [GB] United Kingdom .................. 9511169

[51] Int. Cl.⁶ .................................................. A61M 37/00
[52] U.S. Cl. ............................ 604/82; 604/903; 366/130
[58] Field of Search ..................... 604/89, 82, 90, 604/91, 191, 218, 903; 366/241, 244, 267, 342, 343, 130, 273

[56] References Cited

U.S. PATENT DOCUMENTS

| 4,568,335 | 2/1986 | Updike et al. |
|---|---|---|
| 4,850,966 | 7/1989 | Grau et al. ................................. 604/82 |
| 5,246,670 | 9/1993 | Haber et al. |
| 5,352,036 | 10/1994 | Haber et al. .............................. 366/130 |
| 5,489,266 | 2/1996 | Grimard ................................... 604/89 |
| 5,603,695 | 2/1997 | Erickson .................................. 604/89 |

FOREIGN PATENT DOCUMENTS 235 691  2/1986  Germany.

*Primary Examiner*—John D. Yasko
*Attorney, Agent, or Firm*—Michael T. Bates; David E. Boone

[57] ABSTRACT

A container for a liquid medicament suspension, e.g. an insulin crystal suspension, has a tube with a sealing piston, a cap, and a mixing element which moves along the tube to assist mixing the suspension. The element is guided by the inner surface of the tube and has restricted lateral movement but is free to move axially, for example, by tilting or end to end inversion of the container. Flow passages such as apertures and peripheral recesses are provided in the mixing element which can serve to promote turbulent flow.

The containers are particularly suited for use as multi-dose cartridges for pen-like injection devices or for portable infusion devices which have piston-operating mechanisms to cooperate with the container piston.

12 Claims, 6 Drawing Sheets

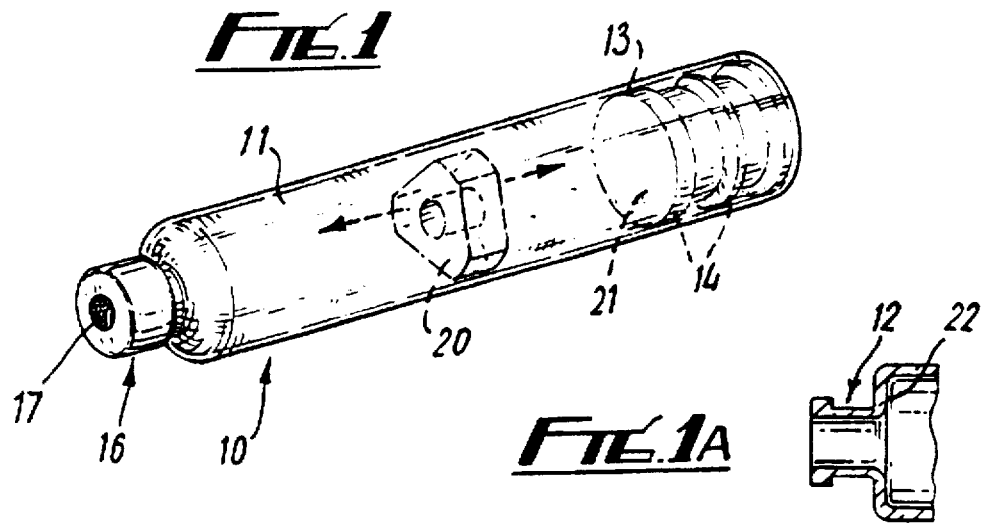
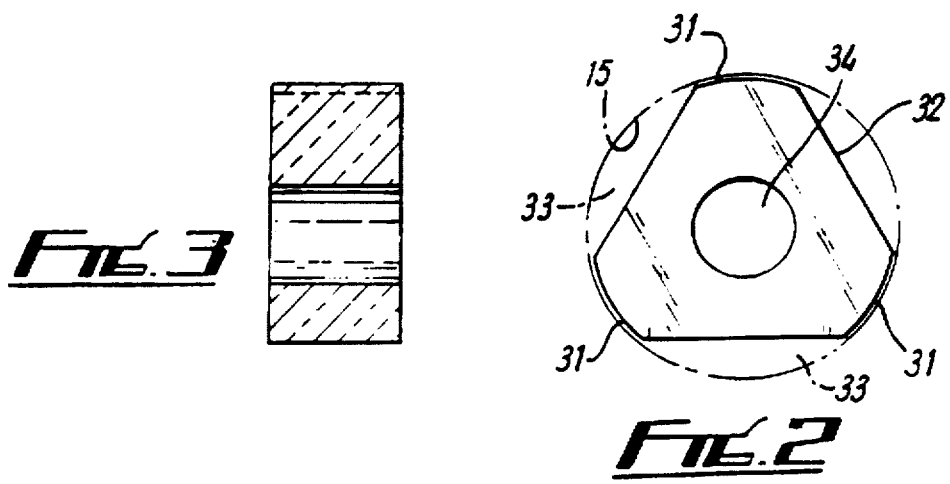
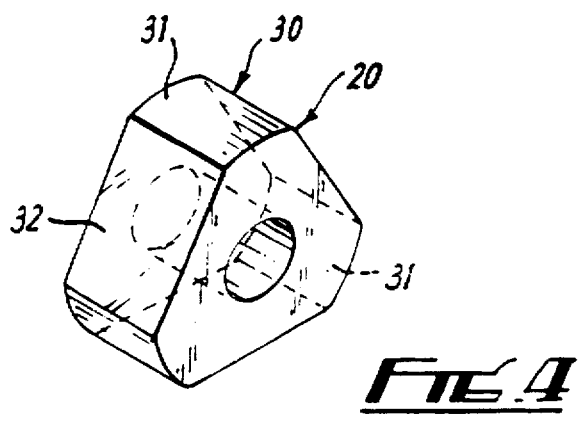

CONTAINERS FOR LIQUID MEDICAMENTS

This invention relates to containers for liquid medicaments, especially for liquid medicament suspensions, that is to say for formulations having liquid and particulate solid components in which at least one of the components, usually at least the solid component, has medicament or medicinal properties.

It is known to provide containers for liquid medicaments, e.g. solutions and suspensions, where the container takes the form of a cartridge or ampoule formed from a tube, suitably of glass, sealed at one end by a piston and terminating at the other end in an outlet piece sealed by a cap. In use, the cartridge is placed in a pen-like device provided with a piston-operating mechanism. This mechanism, when operated, serves to move the piston a predetermined distance along the cartridge tube to eject a dose of the liquid medicament through a hypodermic needle which is attached at the cap end so as to pierce the cap and establish communication with the cartridge interior. The volume of the cartridge is usually sufficient to accommodate several doses of medicament, and the piston-operating mechanism permits individual doses to be administered in controlled and predetermined amounts by the user or patient. Up to several days' supply of medicament may be present in the cartridge. Such a pen-like device and multi-dose cartridges are described in EP-A-0058536. They are especially suited for use with insulin formulations, and diabetic patients value their convenience.

In order to ensure that accurate doses are administered from these cartridge and pen devices, the cartridge, whether containing a suspension or a solution, should be free from any gas bubble, although a small gas bubble or air pocket may be present initially and removed before administration of the first dose by holding the device with the needle pointing upwardly and then expressing any gas by use of the piston-operating mechanism. Instructions on the need and how to do this are normally included in patient information leaflets which accompany the pre-filled cartridges. In the case of liquid medicament suspensions, however, the absence of an air space or gas bubble of any significant size can make it difficult or time-consuming fully to re-suspend the suspension, which will settle out over time as the cartridge/pen rests unused, e.g. in the pocket or handbag of the patient, or during storage of the cartridge before loading into the pen. Re-suspension prior to injection is, of course, essential if the correct dose of the active ingredient, usually the solid component, is to be administered, and failure fully to re-suspend can have dangerous consequences, e.g. in the case of insulin suspensions can lead to coma and other life threatening complications.

It is known to include in such medicament suspension cartridges one or more mixing elements, e.g. as taught in EP-A-0235691. Marketed versions, containing insulin crystal suspensions, include one or more glass or metal spheres which, when the cartridge is shaken or inverted several times, are free to move and roll within the cartridge, thereby facilitating the mixing or homogenisation of the suspension.

Similarly, devices for the controlled infusion of medicaments are known. For example, U.S. Pat. No. 4,568,335 describes such a device which has a container for a medicament suspension, a piston movable along the container, and an outlet piece connected by tubing to a hypodermic needle at an infusion site. Mixing of the suspension is taught to be facilitated by including an air pocket or small steel ball within the container/suspension, which air pocket or ball can be made to move by rotating and inverting the container from end to end several times before infusion of each dose, the action being described as being essential for the safe and effective operation of the device. Again, these devices are disclosed as being particularly suited to the administration of a varied range of insulin suspension formulations, either commercially available or blended extemporaneously with the faster acting solution forms.

The present invention also seeks to address the problem of adequately and quickly re-suspending liquid medicament suspensions in containers such as described above, but further seeks to provide a container which enables yet quicker or more reliable mixing, or with less agitation than is required with the prior disclosed and used mixing elements.

Thus, according to the present invention, there is provided a liquid medicament suspension container, e.g. of the type described above, having a piston operable therein and an outlet therefrom, and containing a solid mixing element, characterised in that the mixing element and the inner surface of the container are shaped to co-operate and constrain the mixing element against significant lateral movement but permit axial movement, the mixing element being shaped to permit flow of suspension from either side of the element to the other as the element moves axially, e.g. on tilting or end to end inversion of the container.

The mixing element is solid in that, unlike an air bubble, the element has a self-determined fixed external shape; however, as mentioned below, the mixing element can be hollow.

The mixing element may be shaped so as to present a continuous or discontinuous peripheral surface co-operating with the inner surface of the container The element may be shaped so as to present and define a plurality of angularly spaced-apart regions, e.g. surfaces or point or line contacts, for cooperation with the container inner surface. In general, and as is preferred, the container and its inner surface will be cylindrical and the overall transverse cross-section of the mixing element will be circular, that is to say the radially outermost parts of the element will lie on a circle. Other correspondingly co-operating shapes are possible for containers of different cross-sectional shape.

The constraint against significant lateral movement of the mixing element within the container is suitably achieved by dimensioning the mixing element appropriately so that it is in a close but freely sliding fit within the container. Some lateral movement is tolerable, but it should not be so great as to enable the mixing element to move significantly out of axial alignment with the container with the undesired result that the element is free to tumble and roll as the container is tilted or inverted or, indeed, to tilt itself out of alignment with the container wall and thereby risk becoming trapped or wedged within the container so that its mixing function is compromised. The mixing element can, however, be free to rotate axially and it may be shaped appropriately to promote or reduce such rotary movement as it slidingly moves within the container.

This is one important difference between the mixing element employed in the present invention and the mixing elements proposed and used in the prior art, i.e. the movement of the element within the container is primarily a sliding movement along the length of the container (optionally with an axial rotary action), rather than being primarily a rolling or tumbling action as in the prior art. Further, and as is preferred, the mixing element of the present invention extends, at least in part, across essentially the full diameter of the container, with the result that a greater proportion of the cross-section of the container is subjected to the sweeping and mixing action of the element as it moves from one end of the container to the other.

The shaping of the mixing element, to permit flow of suspension from one side to the other, suitably takes the form of one or more apertures through the element or, additionally or alternatively, one or more passages defined by the mixing element in combination with the inner surface of the container, such as by recesses or channels formed in the periphery of the mixing element. These apertures, recesses or channels may, if desired, be profiled, e.g. with projections or constrictions, to increase turbulence in the suspension as it flows from either side of the mixing element to the other, and/or they may be angularly disposed relative to the axis of the mixing element and relative to its direction of travel so as to impart an axial rotary motion to the element as it moves axially within the container. Additionally or alternatively, the mixing element may be provided with vanes, e.g. radially disposed vanes, angled with respect to the axis of movement of the element. The vanes may be angled all in the same orientation, so as to cause or promote the mixing element to develop a rotational movement as it moves axially within the container, or may be arranged in opposing orientation to increase turbulence in the flow of the suspension medium as it flows between the vanes.

Where the mixing element is to be caused to move axially within the container by the simple action of tilting or end to end inversion of the latter, the material from which the element is made should have a density sufficiently different from that of the suspension medium, preferably at least a 10% difference, more preferably at least a 50% difference and most preferably at least a 100% difference, to enable the element to fall or rise as the container is so manipulated. Suitable materials which are more dense include metals, such as stainless steel, ceramics, certain plastics and glass, especially sintered glass. Materials less dense than the suspension medium, and which would be buoyant therein, include, for example, certain foamed plastics. Alternatively, the mixing element can be hollow and gas, e.g. air, filled and thereby achieve buoyancy in the suspension medium. Further, the mixing element can be formed of or have implanted therein a magnetic or magnetic responsive material so that the axial movement of the element is caused and controlled by the movement of a correspondingly magnetic device external to the container, such as a slidable collar, e.g. forming a part of any pen-like body in which the container in use is housed. Where the mixing element is magnetic or magnetically responsive, its overall density is less relevant. The material from which the element is made, or at least that part in contact with the suspension medium, should, however, be pharmaceutically acceptable, that is to say be non-toxic and inert to the suspension components.

The material from which the container body is formed is preferably glass, although other pharmaceutically acceptable materials include metals, such as aluminium, rigid plastics materials and ceramics.

The invention may be performed in various ways, and several specific embodiments with possible modifications will now be described by way of example only, with reference to the accompanying drawings, in which:

FIG. 1 is a perspective view of a cylindrical cartridge or ampoule for a liquid medicament suspension and constructed in accordance with the invention;

FIG. 1A is a part-section of the outlet of the cartridge of FIG. 1;

FIG. 2 is an end view of the mixing element;

FIG. 3 is a section through the mixing element of FIG. 2;

FIG. 4 is a perspective view of the mixing element of FIG. 2;

FIGS. 5A to 10A are sections respectively on the lines 5—5, 6—6, 7—7, 8—8, 9—9 and 10—10 of FIGS. 5 to 10;

Figure 5A:

Referring to FIGS. 1 to 4, a container in the form of a single compartment cartridge or ampoule 10 comprises an open-ended cylindrical glass tube 11 which has a reduced diameter neck 12 at one end and which is sealed at the other end by a synthetic rubber piston 13 having, for example, three annular ribs 14 engaging the inner surface of the tube 11.

The cartridge 10 is filled with a liquid medicament suspension, for example an aqueous insulin crystal suspension such as of isophane insulin (NPH), and is free from air bubbles. The neck 12 is closed by an apertured aluminium cap 16 and synthetic rubber membrane or septum 17. When the cartridge 10 is loaded into one of the commercially available pen-like devices and a hypodermic needle is mounted, the needle pierces the membrane or septum 17, thereby entering and communicating with the interior of the cartridge 10.

A mixing element 20 is located in the container and is movable axially in the tube 11 between the inner end 21 of the piston 13 and a shoulder 22 at the inner end of the neck 12 of the outlet.

The element 20 is shaped to co-operate with the inner surface 15 of the tube 11, presenting three angularly spaced-apart surfaces 31 which closely conform to surface 15. The element 20 is dimensioned to be in a close but unrestricted sliding fit in the tube 11 (see especially FIG. 2), thereby being constrained against significant lateral movement. The mixing element 20 is free to rotate about the axis of the tube 11, but the lack of significant lateral movement prevents the element rotating about any other axis so that it is not free to roll or tumble along the tube 11, nor to tilt and become wedged in the tube 11.

The mixing element 20 is also shaped to permit flow of the medicament suspension from one side to the other side by having an aperture 34 extending therethrough, there also being passages 33 extending from one side to the other of the element 20, defined and formed by the three flats 32 on the element 20 in combination with the surface 15 of the tube 11. Either aperture 34 or passages 33 could be omitted, but it is preferred to have at least one inner, e.g. central, and one outer, e.g. peripheral, passage to increase the turbulence produced in the suspension by movement of the mixing element 20 along the tube 11, since it is the turbulence produced in the flow of the suspension medium which is primarily responsible for the stirring action needed to re-suspend the suspension particles leading to the desired homogenisation of the medicament.

The element 20 in this embodiment is made of sintered glass, specifically of Type I (pharmaceutical specification) glass, such as supplied by Schott Glasswerke, Mainz, Germany, under the trade mark "FIOLAX". On tilting of the tube 11 (e.g. when loaded in the pen-like housing) so that its axis lies at an angle of 45° to the horizontal, the mixing element 20 moves within the tube 11 under gravity and due to its greater density than the aqueous suspension, it being guided in its movement by the tube inner surface 15 at three angularly spaced locations defined by the three peripheral portions 31.

In one example, of a container with a capacity of 3.0 cm$^3$ with an overall length of 6.5 cm, where the inner surface 15 has a diameter of 9.5 mm, the portions 31 lie on a diameter of 9 mm, the flats 32 have a length of 5.88 mm, the axial length of element 20 is 4 mm and the diameter of the aperture 34 is 3 mm.

As well as variations in the measurements given above, other variations in the construction of the mixing element (20) are, of course, possible. For example, the peripheral portions can vary in angular extent and can vary also in number. For example, there could be 2, 4, 5 or 6 or more peripheral portions separated by flats. Alternatively, the periphery of the mixing element could present a fully continuous surface, the passages (32) thereby being omitted. Similarly, mixing elements with apertures (34) of different sizes, and of shapes other than circular, may be provided. Also, instead of a single aperture, there may be a plurality of apertures extending through the element (20) or, indeed, there may be an absence of an aperture, provided there are passages (32) present to allow flow of the suspension from either side of the element (20) to the other. Other variations include the provision of transverse ribbing or corrugations on the flats (32) or on the wall of the aperture(s) (34) to increase the turbulence in the flow of the suspension medium. Further, the diameter of the aperture(s) (34) can be varied along the axial length thereof, again to promote increased turbulent flow in the suspension medium. For example, the aperture(s) could taper from one axial end to the other, and where there are, for example, two apertures or more, the direction of the tapers can be reversed as between different apertures. Also, any aperture can be constructed to taper inwards from each axial end to a minimum cross-section, say midway along the element. These variations in different features of the mixing element can, of course, be made independently of the other features. For example, the variations above described with respect to the aperture(s) are equally applicable to mixing elements having different peripheral shapes, e.g. as described below.

A selection of other examples of mixing elements is shown in FIGS. 5 to 10.

Figure 5:
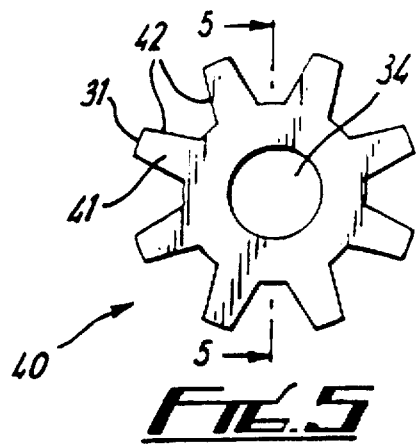
FIGS. 5 to 10 are end views of various differently shaped mixing elements.

In FIGS. 5 and 5A, the mixing element 40 has a single central aperture 34 and eight angularly spaced-apart periphery portions 31 presented on radially disposed teeth 41 having flat sides 42, the angle between adjacent sides 42 of neighbouring teeth being 60°. In one specific example, the surface portions 31 are on a diameter of 9.3 mm, for use in a cartridge with an inner diameter of 9.5 mm.

Figure 6A:
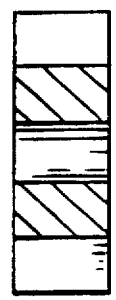
Figure 6:
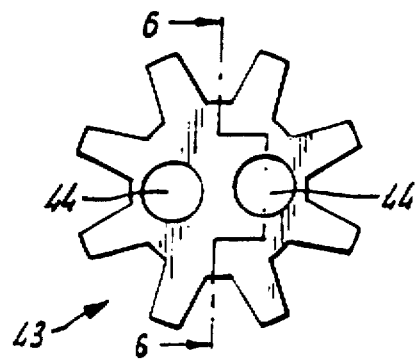

In FIGS. 6 and 6A, the mixing element 43 is similar to mixing element 40 but has two equal sized apertures 44, each of 2 mm diameter.

Figure 7A:
Figure 7:
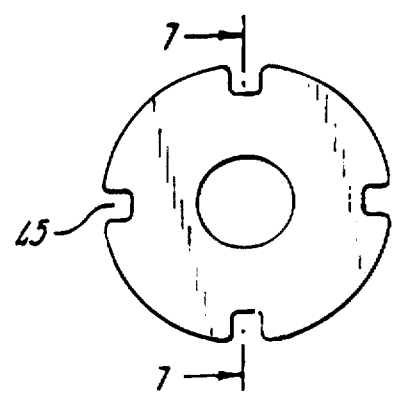

The mixing element shown in FIGS. 7 and 7A is provided with four generally rectangular channels or slots 45 equiangularly spaced around the periphery and which, when the element is located within a cylindrical container, serve to define, with the inner wall surface of the container, passages to allow flow of the suspension from either side of the element to the other. Between the channels or slots 45 are four equiangular periphery portions with surfaces arranged to co-operate with the inner surface of the container. Typically, the channels or slots are 1 mm deep The element is also shown with a single central aperture, but that may be omitted or replaced by two or more apertures.

Figure 8A:
Figure 8:
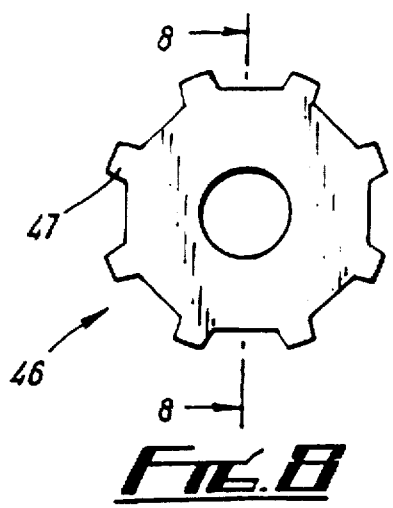

The element 46 in FIGS. 8 and 8A is similar to that in FIGS. 7 and 7A, but the channels are more numerous and each extends over a greater radial arc, with the result that the peripheral portions take on the form of radially disposed teeth 47. Element 46 has a single central aperture therethrough.

Figure 9A:
Figure 9:
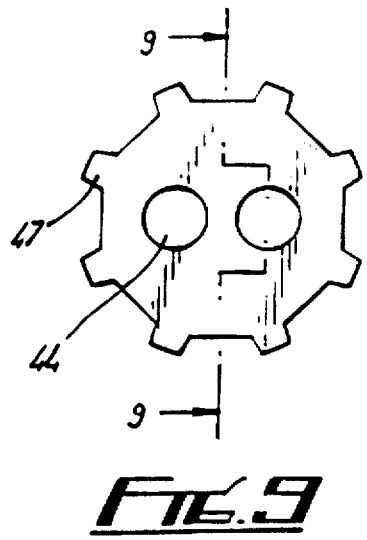

The mixing element of FIGS. 9 and 9A is similar to that of FIGS. 8 and 8A, but is provided with two apertures 44. Although these apertures are shown as having straight bores, the bores may, as described above, be tapered, either in the same or in opposing directions.

Figure 10A:
Figure 10:
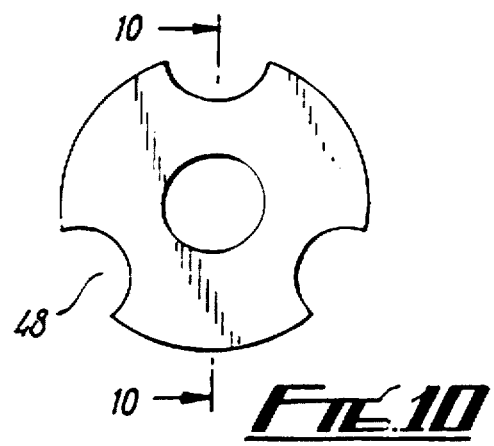

The mixing element illustrated in FIGS. 10 and 10A presents three angularly spaced-apart surfaces shaped to co-operate with the inner surface of a tube shaped container, in similar manner to the surfaces 31 of the mixing element 20 shown in FIGS. 1 to 4, but instead of being separated by flats the co-operating surfaces are separated by part-circular peripheral cut-outs 48, for example of radius 1.5 mm.

Figure 11:
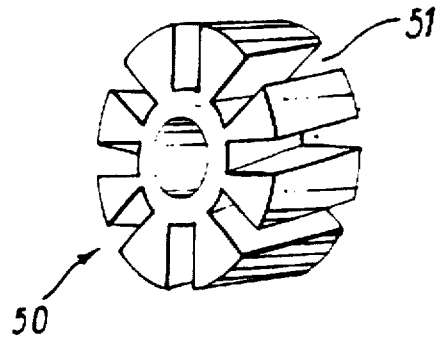
FIGS. 11 and 12 are perspective views of further different mixing elements.
Figure 12:
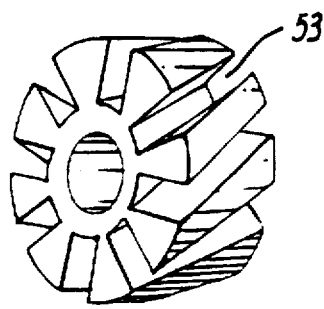

The mixing element 50 shown in FIG. 11, although presenting a plurality of peripheral surfaces to co-operate with the inner surface of a cylindrical cartridge, has deep slots 51 cut into the periphery and which run parallel to the axis of the element and its direction of travel. FIG. 12 shows a similar mixing element but where the slots, although individually straight, are inclined to the central axis of the element and to its direction of travel so as to induce a rotational motion to the element as it moves axially within the cartridge and through the suspension.

Figure 13:
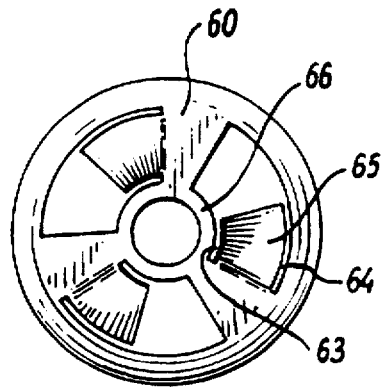
FIGS. 13 and 13A are end and perspective views, respectively, of another element.
Figure 13A:
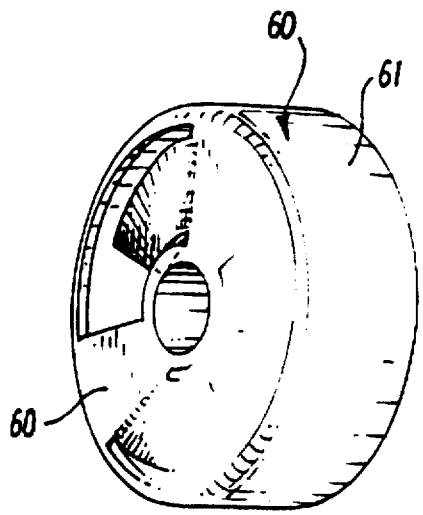
Figure 14:
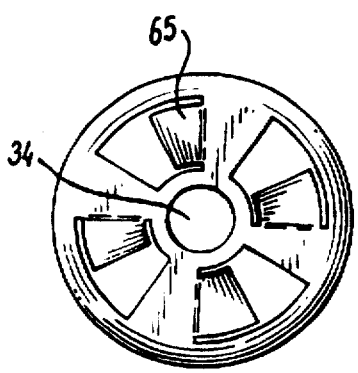
FIG. 14 is an end view of a modified version of the element shown in FIGS. 13 and 13A.

This rotational motion is a characteristic of the mixing element examples shown in FIGS. 13 to 15A. The mixing elements of FIGS. 13 and 14 are of a general cup or dish shape, having a base part 60 and a rim which presents a peripheral outer continuous surface 61 to co-operate with the inner surface of a cylindrical cartridge container. Angularly spaced portions are removed from the base 60 to provide apertures therein, and inner and outer radial slits 63, 64 are cut in the base to enable portions 65 to be bent inwards away from the plane of the base 60. The angular extent of portions 65 can vary, as can the number of such portions—see FIG. 14—and as can also the angle to which the portions are bent from the plane of base 60. The base 60 is connected to an axial tube 66, which defines a central aperture 34.

Figure 15:
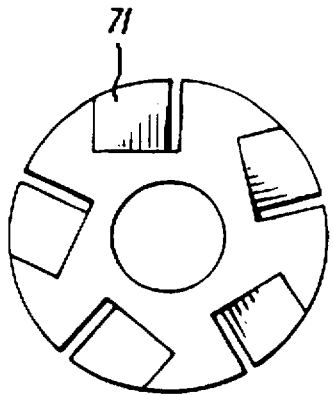
FIGS. 15 and 15A are end and perspective views, respectively, of a further element.
Figure 15A:
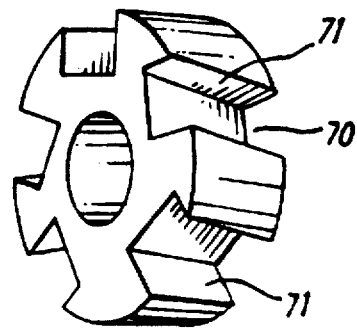

The mixing element shown in FIGS. 15 and 15A is similar to that shown in FIG. 12 with channels 70 whose side faces 71 are inclined at an angle to the axis of the mixing element so that axial movement of the element within the liquid medicament container produces a rotation of the element about its axis. The number of channels and their angle of inclination can be varied.

Figure 16:
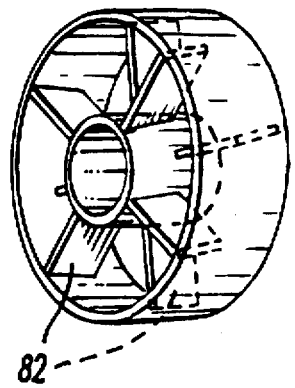
FIGS. 16 and 17 are perspective views of still further elements.
Figure 17:
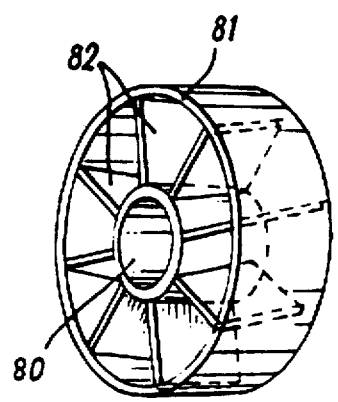

FIGS. 16 and 17 show further turbulence-inducing arrangements within a mixing element. In these embodiments, the mixing elements comprise inner and outer co-axial tubular members, 80 and 81, connected by angularly spaced vanes 82. In FIG. 16, two sets of vanes are shown, one set being both axially and radially displaced from the other. The vanes 82 can be arranged so that their planes are parallel to the axis of tubes 80 and 81 or, if it is desired to induce a rotational movement to the element as it traverses the container, they may be disposed at an angle thereto, in propeller fashion. In order to increase turbulence in the liquid medicament as the element passes, the vanes 82 in each set as shown in FIG. 16 may be disposed at an angle to those in the other set, e.g. at an equal but opposite angle to the axis of the tubes 80 and 81.

It is desirable that the medicament suspension be homogenised to an acceptable degree by the minimum number of passing traverses of the mixing element along the container length, e.g. by tilting or end to end inversion movements of the container, ideally, one or two tilting movements would be required: that is to say, if the cartridge has been stored in a horizontal position, it is desirable that a single tilting in one sense to 45°, accompanied by one full pass of the mixing element in one direction, should produce a suspension of acceptable homogeneity, or, failing that, that a second full pass by reverse tilting the container through 90° should suffice. The desirability of this ease in bringing the suspension into homogeneity is so that patients or users who inadvertently forget to follow the instructions to invert the cartridge/pen a set number of times will, in any event, by their handling of the device and preparing to use it, e.g. by simply removing the device from a pocket, handbag or carrying case and positioning it for injection, e.g. into a thigh, perform sufficient tilting and like manipulative movements with the device as to cause an acceptable level of homogeneity to be reached in the suspension.

The following Comparative Examples illustrate the ease with which insulin crystal suspensions can be homogenised using containers in accordance with the present invention, relative to prior art containers employing simple spherical mixing elements.

COMPARATIVE EXAMPLE 1

In this Example, commercially available 3 ml. cartridges of Basal-H-Insulin 100 (suspension) from Hoechst AG, for use with the Opti-Pen, were used, each having a standard size of 6.5 cm length and inner diameter of 9.5 mm. Half the cartridges were tested as supplied commercially, that is to say containing conventional mixing elements in the form of 3 stainless steel balls, each ball having a diameter of 2.0 mm. The other half were modified by removal of the steel balls and replacement thereof by a single mixing element in accordance with the present invention, made of sintered glass, with a shape according to the element shown in FIGS. 7 and 7A, with an overall diameter of 9.0 mm, axial length (thickness) 4.5 mm, central aperture diameter 3.0 mm, and in which each of the four peripheral, axially extending grooves or channels has a width of 1.0 mm and a depth of 1.0 mm.

In each of the following tests, 3 cartridge samples from each set were used.

Test 1a

In this first test, the cartridges were stored for 12 hours in the upright position, that is to say vertically with the outlet necks uppermost. After this storage, each cartridge was carefully transferred, whilst maintaining the storage orientation, to a test machine electronically controlled and adjusted to invert each cartridge through 180° over a 1.5 second period, and to repeat that action until stopped. The degree of homogenisation was monitored visually and assessed on a percentage basis, and the number of inversions noted.

Test 2a

In this second test, the above procedure of Test 1 was followed, except that the cartridges were stored and carefully transferred to the test machine in inverted orientation, that is to say vertically with their outlet necks lowermost. Again, the degree of homogenisation was assessed and the number of inversions noted.

Test 3a

In this third test, the cartridges were each stored for 12 hours in the horizontal position, then carefully transferred to the test machine in that position. In this test, the machine was controlled to tilt each cartridge through an angle of 45° (over 0.8 second), then back to the horizontal (0.8 sec.) and then to a position at 45° to the horizontal in the opposite direction (0.8 sec.). Again, this action was repeated, visual assessment made of the degree of homogenisation, and the number of tilts (to a 45° angle and back to horizontal being a single tilt) noted.

Test 4a

In this fourth test, the procedure of Test 3, above, was repeated, except that the machine was programmed to tilt each cartridge from the horizontal through an angle of 90° (over 1.5 sec.), back to the horizontal (1.5 sec.), and then through 90° (1.5 sec.) in the opposite direction to the first movement. The machine repeated this action until stopped, and again the degree of homogenisation was assessed and the number of tilts (one 90° degree and back to horizontal movement being a single tilt) noted.

The results of these Tests are shown in the following Table 1.

TABLE 1

| TEST No | Mixing Element | Number of Cartridge Inversions/Tilts | Average Degree of Homogenisation |
|---|---|---|---|
| 1a | 3 × 2.0 mm. steel balls | 20 | Incomplete, max 50% |
| 1a | Element of invention | 3 | Complete. 100% |
| 2a | 3 × 2.0 mm. steel balls | 20 | Incomplete, max 50% |
| 2a | Element of invention | 3 | Complete. 100% |
| 3a | 3 × 2.0 mm. steel balls | 20 | Incomplete, max 40% |
| 3a | Element of invention | 2 | Complete. 100% |
| 4a | 3 × 2.0 mm. steel balls | 20 | Incomplete, max 50% |
| 4a | Element of invention | 3 | Complete. 100% |

COMPARATIVE EXAMPLE 2

In this Example, commercially available 3 ml. Insulin Protamin HM Penfil cartridges (suspension), from Novo-Nordisk, were used, again of standard 6.5 cm length and 9.5 mm internal diameter. Half were tested as supplied commercially, that is to say containing a conventional mixing element in the form of a glass bead having a diameter of 2.5 mm, and the other half were modified by removal of the glass bead and replacement with a mixing element according to the invention, as used in Comparative Example 1, above.

Tests 1b to 4b were then carried out in identical manner to Tests 1a to 4a, above, there again being 3 cartridges in each batch tested, and again the average degree of homogenisation was visually assessed and the number of inversions/tilts noted. The results are set out in the following Table 2.

TABLE 2

| TEST No | Mixing Element | Number of Cartridge Inversions/ Tilts | Average Degree of Homogenisation |
|---|---|---|---|
| 1b | 1 × 2.5 mm. glass bead | 20 | Incomplete, max 50–60% |
| 1b | Element of invention | 3 | Complete 100% |
| 2b | 1 × 2.5 mm. glass bead | 20 | Incomplete, max 50–60% |
| 2b | Element of invention | 3 | Complete 100% |
| 3b | 1 × 2.5 mm. glass bead | 20 | Incomplete, max 50–60% |
| 3b | Element of invention | 3 | Complete 100% |
| 4b | 1 × 2.5 mm. glass bead | 20 | Incomplete, max 50–60% |
| 4b | Element of invention | 3 | Complete 100% |

I claim:

1. A container for a liquid medicament suspension having a piston operable therein and an outlet therefrom, and containing a solid mixing element, wherein the mixing element and the inner surface of the container are shaped to co-operate and constrain the mixing element against significant lateral movement but permit axial movement, the mixing element being shaped to permit flow of suspension from either side of the element to the other as the element moves axially.

2. A container as claimed in claim 1, wherein the mixing element is shaped so as to present and define a plurality of angularly spaced-apart regions for co-operation with the inner surface of the container.

3. A container as claimed in claim 1, wherein the mixing element is constrained against significant lateral movement within the container by being dimensioned so as to be in a close but sliding fit within the container.

4. A container as claimed in claim 1, wherein the mixing element is free to rotate axially.

5. A container as claimed in claim 1, wherein the mixing element, in order to permit flow of suspension from either side of the element to the other, is provided with means defining one or more apertures extending through the element, and/or with one or more passages defined by the element in combination with the inner surface of the container.

6. A container as claimed in claim 5, wherein the passages are partly defined by recesses or channels formed in the periphery of the element.

7. A container as claimed in claim 6, wherein the apertures, recesses or channels are profiled with projections or constrictions to increase turbulence in the suspension as the suspension flows from either side of the mixing element to the other.

8. A container as claimed in claim 7, wherein the apertures, recesses or channels are angularly disposed relative to the axis of the mixing element so as to impart an axial rotary motion to the element as it moves axially within the container.

9. A container as claimed in claim 1, wherein the container and the inner surface thereof is cylindrical and the overall transverse cross-section of the mixing element is circular.

10. A container as claimed in claim 1, wherein the mixing element is made of metal, ceramic, plastics material or glass.

11. A container as claimed in claim 1, wherein the mixing element is buoyant in the suspension medium.

12. A container as claimed in claim 1, wherein the mixing element is caused to move axially within the container, by the action of tilting or end to end inversion of the container.

* * * * *